(12) United States Patent
Willard et al.

(10) Patent No.: US 7,326,195 B2
(45) Date of Patent: Feb. 5, 2008

(54) TARGETED COOLING OF TISSUE WITHIN A BODY

(75) Inventors: Martin Willard, Burnsville, MN (US); Kent Harrison, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 289 days.

(21) Appl. No.: 10/715,636

(22) Filed: Nov. 18, 2003

(65) Prior Publication Data
US 2005/0107741 A1    May 19, 2005

(51) Int. Cl.
*A61M 31/00* (2006.01)
(52) U.S. Cl. .................................. 604/508; 604/113
(58) Field of Classification Search ............. 604/113, 604/6.401, 6.13–6.16, 96.01, 102.01–102.03, 604/264, 500, 506–509; 607/102
See application file for complete search history.

(56) References Cited

U.S. PATENT DOCUMENTS

| | | | |
|---|---|---|---|
| 5,011,469 | A | 4/1991 | Buckberg et al. |
| 5,624,392 | A | 4/1997 | Saab |
| 5,837,003 | A | 11/1998 | Ginsburg |
| 5,957,963 | A | 9/1999 | Dobak, III |
| 5,989,238 | A * | 11/1999 | Ginsburg .................. 604/500 |
| 6,033,383 | A | 3/2000 | Ginsburg et al. |
| 6,042,559 | A | 3/2000 | Dobak, III |
| 6,044,845 | A | 4/2000 | Lewis |
| 6,096,068 | A | 8/2000 | Dobak, III et al. |
| 6,113,584 | A * | 9/2000 | Morley et al. ............. 604/500 |
| 6,149,676 | A | 11/2000 | Ginsburg |
| 6,149,677 | A | 11/2000 | Dobak, III |
| 6,161,543 | A | 12/2000 | Cox et al. |
| 6,223,085 | B1 | 4/2001 | Dann et al. |
| 6,231,595 | B1 | 5/2001 | Dobak, III |
| 6,261,312 | B1 | 7/2001 | Dobak, III et al. |

(Continued)

FOREIGN PATENT DOCUMENTS

WO    WO 01/60441    8/2001

(Continued)

OTHER PUBLICATIONS

Dae et al., "Effect of endovascular cooling on myocardial temperature, infarct size, and cardiac output in human-sized pigs," *Am. J. Physiol. Heart Circ. Physiol.*, 2002, 282:H1584-H1591.

(Continued)

*Primary Examiner*—Nicholas Lucchesi
*Assistant Examiner*—Theodore J Stigell
(74) *Attorney, Agent, or Firm*—Fish & Richardson P.C.

(57) ABSTRACT

Devices and methods to cool a target tissue region inside the body are described. Fluid cooled below normal body temperature and blood at a normal body temperature are provided to the tissue region in proportions to cool the tissue region. A system for controlling the temperature of the target tissue region is disclosed. The system includes a catheter and a control system that controls the amount of cool fluid and blood provided to the tissue region. A catheter for providing cool fluid to the tissue region is also provided. The catheter includes a temperature sensor that extends to a location distal to the distal end of the catheter to sense the temperature of the tissue region.

28 Claims, 6 Drawing Sheets

U.S. PATENT DOCUMENTS

| | | | |
|---|---|---|---|
| 6,295,990 B1* | 10/2001 | Lewis et al. | ............... 128/898 |
| 6,325,818 B1 | 12/2001 | Werneth | |
| 6,481,439 B1 | 11/2002 | Lewis et al. | |
| 6,497,721 B2 | 12/2002 | Ginsburg et al. | |
| 6,508,777 B1 | 1/2003 | Macoviak et al. | |
| 6,527,798 B2 | 3/2003 | Ginsburg et al. | |
| 6,589,271 B1 | 7/2003 | Tzeng et al. | |
| 6,607,517 B1* | 8/2003 | Dae et al. | ................... 604/500 |
| 6,610,083 B2 | 8/2003 | Keller et al. | |
| 6,620,188 B1 | 9/2003 | Ginsburg et al. | |
| 6,645,234 B2 | 11/2003 | Evans et al. | |
| 6,648,908 B2 | 11/2003 | Dobak, III et al. | |
| 6,908,462 B2 | 6/2005 | Joye et al. | |
| 2001/0001832 A1 | 5/2001 | Dobak et al. | |
| 2001/0047196 A1 | 11/2001 | Ginsburg et al. | |
| 2002/0111616 A1 | 8/2002 | Dea et al. | |
| 2002/0120314 A1 | 8/2002 | Evans et al. | |
| 2002/0128568 A1 | 9/2002 | Mooney et al. | |
| 2002/0161351 A1 | 10/2002 | Samson et al. | |
| 2003/0014094 A1 | 1/2003 | Hammack et al. | |
| 2003/0060762 A1 | 3/2003 | Zvuloni et al. | |
| 2003/0216688 A1 | 11/2003 | Huybregts et al. | |
| 2004/0167467 A1* | 8/2004 | Harrison et al. | ............ 604/113 |
| 2004/0215177 A1 | 10/2004 | Swanson | |

FOREIGN PATENT DOCUMENTS

| | | |
|---|---|---|
| WO | WO 02/58605 | 8/2002 |
| WO | WO 03/086253 | 10/2003 |
| WO | WO 2004/075747 | 9/2004 |

OTHER PUBLICATIONS

Dave et al., "Hypothermic, Closed Circuit Pericardioperfusion: A Potential Cardioprotective Technique in Acute Regional Ischemia," *J. Am. Coll. Cardiol.*, 1998, 31(7):1667-1671.

Dixon et al., "Induction of Mild Systemic Hypothermia With Endovascular Cooling During Primary Percutaneous Coronary Intervention for Acute Myocardial Infarction," *J. Am. Coll. Cardiol.*, 2002, 40:1928-1934.

Hale et al., "Regional hypothermia reduces myocardial necrosis even when instituted after the onset of ischemia," *Basic Res. Cardiol.*, 1997, 92:351-357.

Hale et al., "Myocardial temperature in acute myocardial infarction: protection with mild regional hypothermia," *Am. J. Physiol.*, 1997, 273:H220-H227.

Schwartz et al., "Regional Topical Hypothermia of the Beating Heart: Preservation of Function and Tissue," *Ann. Thorac. Surg.*, 2001, 72:804-809.

Wakida et al., "Percutaneous Cooling of Ischemic Myocardium by Hypothermic Retroperfusion of Autologous Arterial Blood: Effects on Regional Myocardial Temperature Distribution and Infarct Size," *J. Am. Coll. Cardiol.*, 1991, 18:293-300.

* cited by examiner

TARGETED COOLING OF TISSUE WITHIN A BODY

TECHNICAL FIELD

This invention relates to cooling a target tissue region inside a body.

BACKGROUND

Myocardial ischemia, and in severe cases acute myocardial infarction (AMI), can occur when there is inadequate blood circulation to the myocardium due to coronary artery disease. Evidence suggests that early reperfusion of blood into the heart, after removing a blockage to blood flow, dramatically reduces damage to the myocardium. However, the reestablishment of blood flow into the heart may cause a reperfusion injury to occur. Reperfusion injury is believed to be due to the build up of waste products on the myocardium during the time blood flow was inadequate and the reaction of these waste products with oxygen in the blood when normal blood flow is reestablished. It is possible to reduce reperfusion injury to the myocardium by cooling the myocardial tissue prior to reperfusion. Mild cooling of the myocardial tissue to a temperature between 28 and 36 degrees Celsius provides a protective effect, likely by the reduction in the rate of chemical reactions and the reduction of tissue activity and associated metabolic demands.

One method of cooling myocardial tissue is to place an ice pack over the patient's heart. Another method involves puncturing the pericardium and providing cooled fluid to a reservoir inserted into the pericardial space near the targeted myocardial tissue. Cooling of the myocardial tissue may also be accomplished by perfusing the target tissue with cooled solutions. A catheter having a heat transfer element located in the catheter's distal tip may also be inserted into a blood vessel to cool blood flowing into and through the heart. It is also possible to cool the myocardial tissue by supplying cool blood to the heart through a catheter placed in the patient's coronary sinus.

SUMMARY

The invention features devices and methods to cool a target tissue region inside the body. In an aspect, the invention features a method of cooling a target tissue region that includes providing fluid cooled below normal body temperature and blood at a normal body temperature to the tissue region in proportions to cool the tissue region and maintain, for an extended period of time, the temperature of the tissue region within a target temperature range that is below normal body temperature.

Implementations may include providing the cooled fluid and the blood at normal body temperature to the tissue region simultaneously. The providing of the blood at normal body temperature to the tissue region may be performed using a catheter that occludes a vessel upstream from the tissue region and permits a selected amount of blood to flow through a lumen in the catheter and to the tissue region. The catheter may also perform the providing of cool fluid to the tissue region. The providing of blood to the tissue region can be performed by occluding a vessel upstream from the tissue region to restrict normal blood flow and then removing the occlusion to permit normal blood flow. A catheter may also provide blood to the tissue region by partially occluding a vessel in fluid communication with the tissue region to permit a restricted amount of blood to flow to the tissue region. In other implementations, a catheter positioned in a vessel in fluid communication with the tissue region may provide the fluid to the tissue region through a lumen that extends longitudinally through the catheter, the lumen having a diameter of at least twenty thousandths of an inch.

In another aspect, the invention features a method of cooling a target tissue region inside a body that includes occluding a body vessel to prevent normal blood flow to the tissue region. While the body vessel is occluded, cooled fluid is provided to the tissue region to cool the tissue region below normal body temperature. Normal blood flow to the tissue region is recommenced by removing the occlusion in the body vessel. Normal blood flow to the tissue region is prevented again by occluding the body vessel before the temperature of the tissue region returns to normal body temperature. While the body vessel is occluded, cooled fluid is provided to the tissue region again to maintain the temperature of the tissue region below normal body temperature.

In implementations, the body vessel may be occluded to prevent normal blood flow to the tissue region by inflating a balloon positioned in the vessel. In addition, a catheter positioned in a vessel at a location upstream from the tissue region may provide the fluid to the tissue region through a lumen extending longitudinally through the catheter, the lumen having a diameter of at least twenty thousandths of an inch.

In another aspect, the invention features a method of cooling a target tissue region inside a body that includes restricting normal blood flow to the tissue region so that only a desired amount of blood is provided to the tissue region. Cool fluid is provided to mix with the blood provided to the tissue region so as to cool the tissue region below normal body temperature and to maintain, for an extended period of time, the temperature of the tissue region within a target tissue range that is below normal body temperature.

In implementations, the providing of the blood at normal body temperature to the tissue region can be performed using a catheter that occludes a vessel upstream from the tissue region and permits a selected amount of blood to flow through a lumen in the catheter and to the tissue region. The providing of blood at normal body temperature to the tissue region may also be performed using a catheter to partially occlude a vessel upstream from the tissue region and permit a selected amount of blood to reach the tissue region. In other implementations, a catheter positioned in a vessel in fluid communication with the tissue region may provide the fluid to the tissue region through a lumen that extends longitudinally through the catheter, the lumen having a diameter of at least twenty thousandths of an inch.

Implementations of the various aspects of the invention may include one or more other features. For example, the tissue region may be maintained within the target temperature range that is below normal body temperature for a time period beyond the normal length of time a tissue region is deprived of oxygenated blood during a heart procedure, or about two minutes. The temperature of the tissue region can be within a target temperature range of about 28 to 36 degrees Celsius. In addition, the providing of fluid and blood to cool the target tissue region can be performed during a procedure to open a lesion in a vessel. Further, a control system may control the providing of fluid and blood to the tissue region to maintain the temperature of the tissue region below normal body temperature.

In another aspect, the invention features a system for controlling the temperature of a target tissue region inside the body. The system includes a catheter for providing cooled fluid to the tissue region and for controlling normal blood flow to the tissue region. The system also includes a control system that controls the amount of the cooled fluid and blood that the catheter provides to the tissue region so as to cool and to maintain, for an extended period of time, the tissue region within a target temperature range that is below normal body temperature.

Implementations may include one or more of the following. The catheter for providing fluid and controlling normal blood flow to the tissue region may be a perfusion catheter. The catheter for providing fluid and controlling normal blood flow to the tissue region may also be a balloon catheter. The catheter may include an infusion lumen for providing fluid to the tissue region that has a diameter of at least twenty thousandths of an inch. The catheter may also include a temperature sensor that may be advanced to a location distal to the catheter to measure the temperature of the tissue region.

The control system may include a controller that controls the cooling of the tissue region without measuring the temperature of the tissue region. The control system may also include a controller that controls the cooling of the tissue region without measuring the temperature of the cool fluid as it exits the catheter and is provided to the tissue region. In addition, the system may have a temperature monitor that receives temperature information from a temperature sensor of the catheter. In other implementations, the control system may include an infusion pump to control the amount of cool fluid provided to the tissue region. An inflation pump to inflate and deflate a balloon on the catheter may also be provided.

In another aspect, the invention features a catheter for providing cool fluid to a tissue region inside a body. The catheter includes an elongated member having a lumen extending longitudinally therethrough to a distal end of the elongated member and a temperature sensor that extends to a location distal to the distal end of the elongated member to sense the temperature of the tissue region.

In implementations, the temperature sensor may be a thermocouple that has two conductors of different material extending from a proximal end of the catheter and joined at a distal end to form a junction. The temperature sensor may sense the temperature of the tissue region by measuring the temperature of a vessel wall located distal to the distal end of the elongated member and adjacent to the target tissue region. In other implementations, the temperature sensor may sense the temperature of the tissue region by measuring the temperature of the cool fluid provided to the tissue region distal to the distal end of the elongated member and adjacent to the target tissue region.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

When an area of tissue has been deprived of oxygenated blood, such as during acute myocardial infarction (AMI), the tissue region becomes ischemic. The methods illustrated herein may be used to reduce the injury to the ischemic tissue associated with reperfusion by providing cool fluid and blood at normal body temperature (typically 37 degrees Celsius) to the ischemic tissue region in proportions to cool and maintain the temperature of the ischemic tissue region below normal body temperature for an extended period of time. By providing both cool fluid and normal blood flow to the tissue region, reperfusion injury can be reduced without extending the time that the tissue region is deprived of oxygen.

Figure 1A:
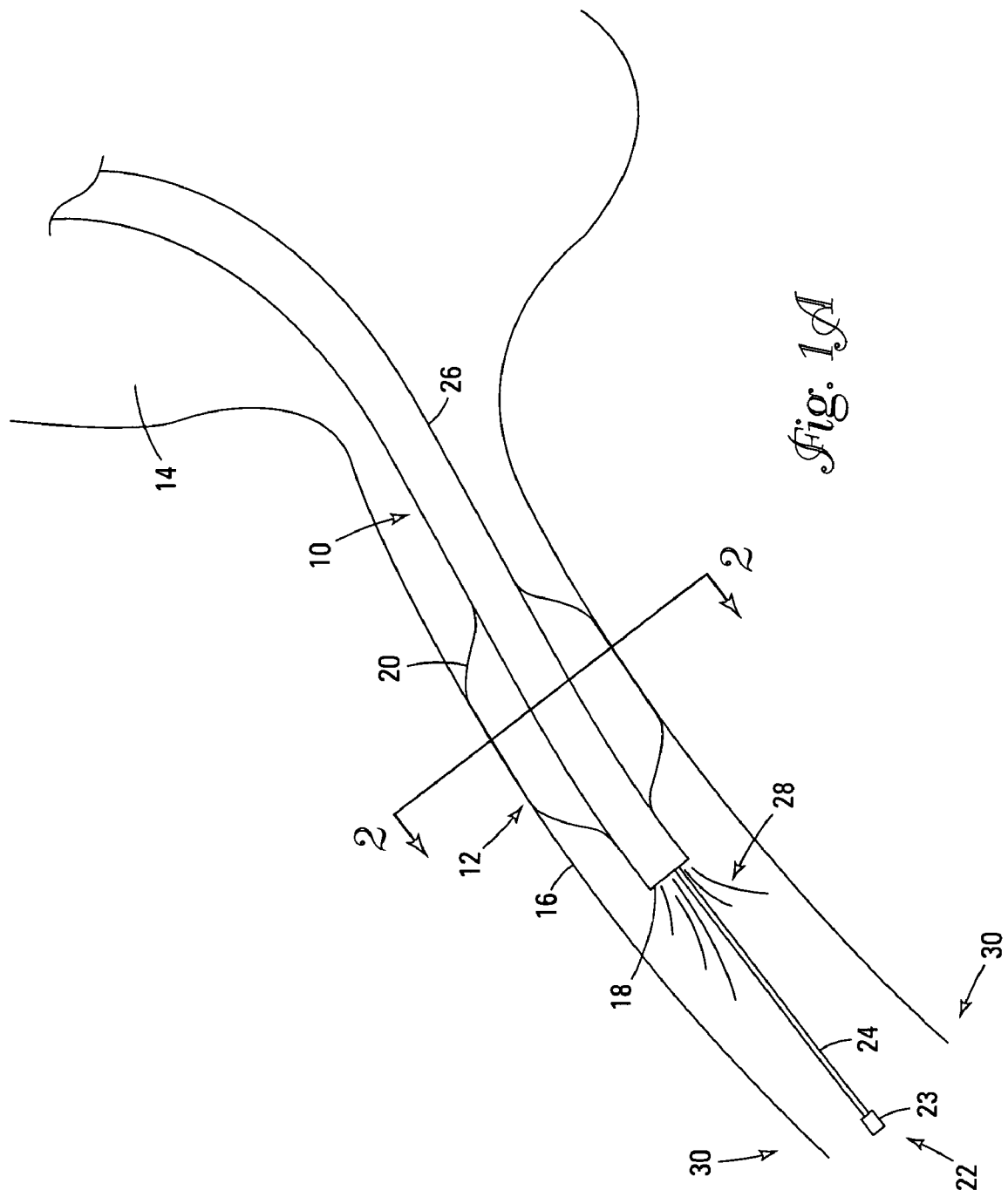
FIGS. 1A and 1B are diagrams showing a side view of a distal end of a balloon catheter positioned in a coronary artery, shown in cross-section, and illustrate a method of cooling a target tissue region in the heart.
Figure 1B:
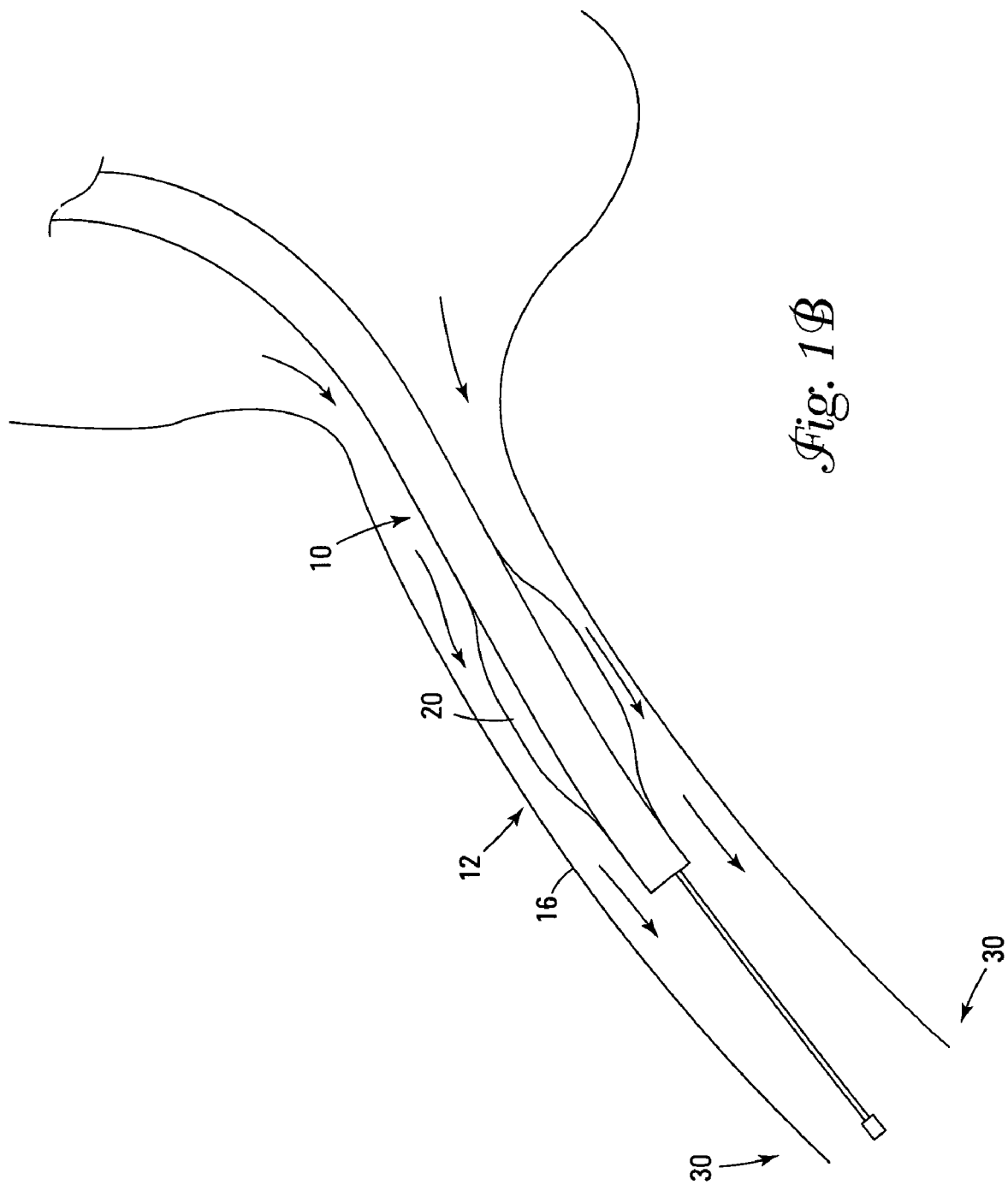

FIGS. 1A and 1B illustrate a method of cooling a target tissue region located within the heart. Referring to FIG. 1A, a distal portion 10 of a conventional balloon catheter is shown inside a coronary artery 16 of a patient's heart. Once positioned in the coronary artery 16, a balloon 20 at the catheter's distal end 12 may be inflated to occlude the artery 16 and prevent normal blood flow to a target tissue region 30. In some implementations, the inflation of balloon 20 opens an occlusion in the coronary artery 16. After normal blood flow has been stopped, cool fluid 28, such as saline or ringers lactate, may be introduced into the coronary artery 16 to cool the tissue region 30. Once the tissue region 30 is cooled to a desired temperature, for example twenty-eight degrees Celsius, the balloon 20 may be deflated to resume normal blood flow through the coronary artery 16 as shown in FIG. 1B. The flow of blood provides oxygen to the tissue region, and in addition, increases the temperature of the tissue. To maintain the temperature of the tissue region 30 within a desired range for an extended period of time, the cooling method of FIGS. 1A and 1B may be repeated as required.

The catheter's distal end 12 may be positioned inside the coronary artery 16 as shown in FIG. 1A by inserting the catheter's distal end 12 into a vessel, such as the femoral artery, that provides access to the patient's aorta 14. A guidewire (not shown) is advanced through the aorta 14 and into the desired vessel, which in the FIG. 1A example is coronary artery 16. The catheter's distal end may then be advanced over the wire through the aorta 14 and into the coronary artery 16. In some implementations, a guide catheter may also be used to guide the catheter through the vessel.

The catheter 10 has an inflation lumen (not shown) that extends longitudinally through the inside of the catheter 10 from the balloon 20 to the catheter's proximal end (not shown in FIGS. 1A and 1B). An inflation medium (gas or liquid) may be provided to and removed from the balloon 20 via the inflation lumen to inflate and deflate the balloon 20. In this implementation, the balloon 20 is a conventional balloon suited for use in heart vessels. For implementations in other locations inside the body, a different balloon may be used. The inflation and deflation of the balloon 20 may be controlled manually by the physician, or in some implementations, may be controlled automatically by a control system located outside of the patient's body, as will be described later.

An infusion lumen (the lumen being shown in FIG. 2) extends longitudinally through the catheter 10 from an opening 18 at the catheter's distal end 12 to an opening at the catheter's proximal end (not shown in FIGS. 1A and 1B). The cool fluid 28 is provided to the coronary artery 16 via the catheter's infusion lumen and then distributed to the tissue region 30. The cool fluid may be provided at various temperatures and infusion rates, as will be described in conjunction with FIG. 3. The providing of the cool fluid 28 may be performed manually by a physician or under the control of a control system.

In the FIG. 1A example, the catheter's infusion lumen may have a diameter at its distal end 12 of either eighteen or twenty thousandths of an inch, which is larger than the sixteen thousandths diameter that is typically used in heart procedures. The use of this larger diameter infusion lumen allows the cool fluid 28 to be provided to the tissue region 30 at higher infusion rates without producing a "jetting" effect. The jetting effect occurs when fluid 28 is expelled from the catheter's opening 18 at flow rates that are likely to cause damage to the vessel walls. By increasing the diameter of the lumen from sixteen thousandths to, for example, twenty thousandths, the flow velocity may be reduced by approximately one-third. In implementations where catheters with infusion lumen diameters smaller than twenty thousandths of an inch are used, the infusion rate of the fluid 28 may need to be reduced to prevent jetting.

A temperature sensor 22 is located near the catheter's distal end 12 to sense the temperature of the cool fluid 28 that is provided to the tissue region 30 through the opening 18. The temperature sensor provides feedback to the physician performing the procedure or to an external control system that may be used to more precisely control the cooling of the tissue region 30. In the illustrated example, the temperature sensor 22 is a thermocouple. The thermocouple is made up of two conductive wires (shown as a single wire 24 in FIGS. 1A and 1B for clarity) of dissimilar materials that are insulated from each other. At a distal end, the wires 24 are connected together to form a junction 23 that serves as a sensing element. This junction 23 produces a voltage difference that is dependent on the temperature of the junction 23. The wires 24 extend proximally from the junction 23, through an opening in the distal end of the shaft, and through a lumen in the catheter shaft 26 to an opening at the catheter's proximal end. An external device may be connected to proximal ends of the two thermocouple wires 24 to measure the voltage difference between the wires 24, and then convert that voltage measurement into an indication of the temperature of the junction 23.

In one example, the wires 24 are approximately two thousands of an inch in diameter and may extend through the catheter's infusion lumen. Alternatively, the wires 24 may extend through an additional smaller lumen that extends longitudinally through the catheter's shaft 26 that is sized specifically for the temperature sensor (both lumens shown in FIG. 2). The temperature sensor 22 may also be placed at different locations within the catheter to measure the temperature of the fluid 28 being provided to tissue region 30 (not shown). Alternatively, the temperature sensor 22 may be advanced distal to the catheter as shown in FIG. 1A. Positioning the temperature sensor 22 into the coronary artery in this manner may allow the temperature of the tissue region 30 to be determined more precisely by providing the temperature of the fluid 28 or the tissue in the coronary artery 16 near the tissue region 30.

In other implementations, other temperature sensors may be used, such as thermistors or other suitable temperature sensing mechanisms. Instead of extending through the infusion lumen or guide wire lumen in the catheter, the wires 24 may extend through an additional lumen in the catheter shaft 26. Alternatively, the temperature sensor 22 may be omitted.

Figure 2:
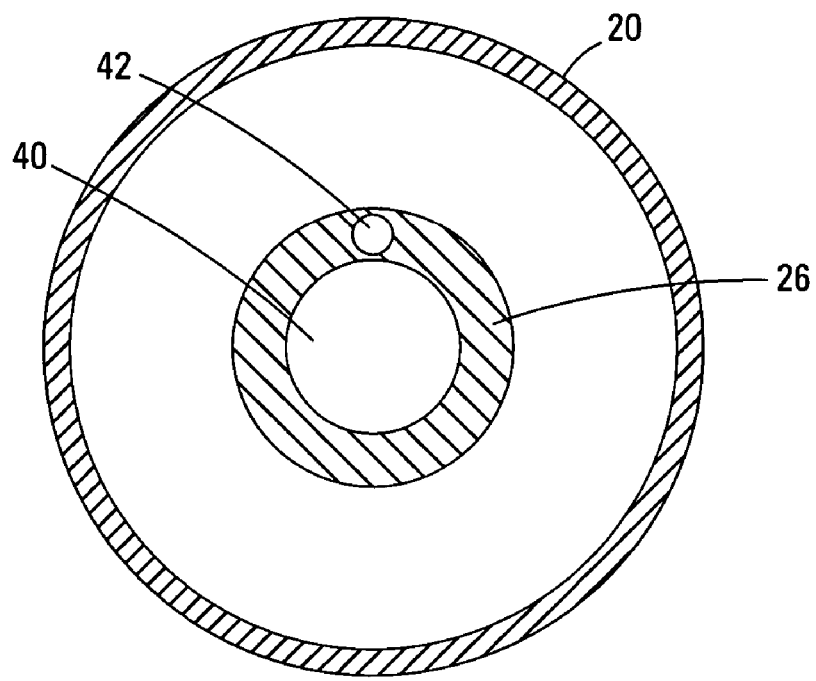
FIG. 2 is a cross-sectional view of the balloon catheter along the line 2-2 shown in FIG. 1A.

FIG. 2 is a cross-sectional view of the balloon catheter along the line 2-2 shown in FIG. 1A. The FIG. 2 cross-section illustrates the relative diameters of the lumens that extend longitudinally through the catheter and the catheter's inflated balloon 20. In the FIG. 2 example, the catheter includes an infusion lumen 40 and a sensor lumen 42. The infusion lumen may have a diameter of twenty thousandths of an inch, which would allow a physician to use an eighteen-thousandths guidewire, or a smaller guidewire if desired. In other examples, the infusion lumen 40 may have a diameter of eighteen thousandths of an inch or smaller. The sensor lumen 42 may be approximately two thousandths of an inch in diameter to permit the passage of the temperature sensor wires through the catheter. The outer diameter of the catheter shaft 26 may be approximately twenty-five thousands of an inch. However, the catheter shaft 26 may be larger in other examples. The outer diameter of the inflated balloon 20 may be approximately three millimeters in diameter. In implementations outside of the heart, a catheter having a larger diameter shaft 26 and balloon 20 may be used.

Figure 3:
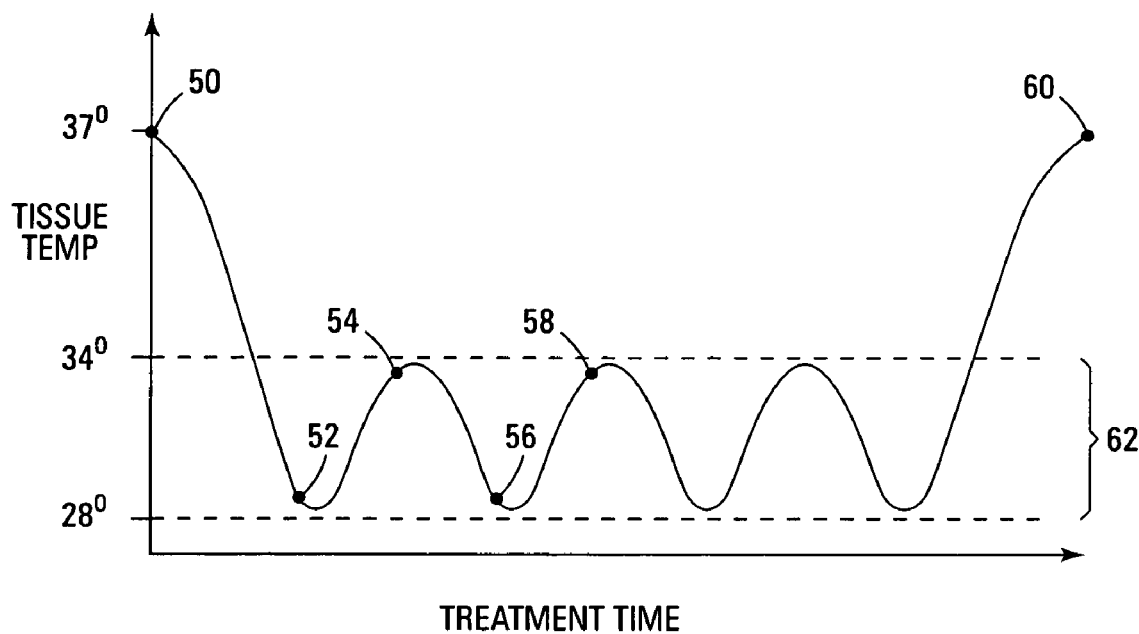
FIG. 3 is a graph that shows the temperature of the target tissue region during the application of the cooling method illustrated in FIGS. 1A and 1B.

With the aid of FIG. 3, the coordination of the inflation and deflation of the balloon 20, which controls normal blood flow in the coronary artery 16 and the providing of cool fluid 28 to the tissue region 30 will be described. FIG. 3 is a graph that illustrates the temperature of the target tissue region over time, namely, during the application of the cooling method of FIGS. 1A and 1B. The FIG. 3 graph is not based on actual results, but rather is intended to illustrate the cooling method more clearly. Before the cooling process is started, the temperature of the target tissue region is approximately thirty-seven degrees Celsius (normal body temperature), which is indicated by data point 50 on the FIG. 3 graph. In this example, the tissue region is maintained between twenty-eight and thirty-four degrees Celsius, which is referred to as the target temperature range 62.

Once the distal end of the catheter is positioned in the coronary artery and the guidewire is removed, the cooling process begins by inflating the balloon at data point 50 to prevent normal blood flow to the target tissue region. After the balloon has occluded the coronary artery, cool fluid is provided to the tissue region (as shown in FIG. 1A). In this example, the cool fluid is provided at a temperature of approximately fifteen degrees Celsius and at an infusion rate of twenty-five ml/min. The providing of cool fluid cools the tissue from normal body temperature to the low temperature in the target temperature range 62, twenty-eight degrees Celsius, as indicated by data point 52.

During the initial cooling of the tissue between data points 50 and 52, the coronary artery is occluded by the balloon and the tissue continues to be deprived of oxygenated blood. At the fluid temperature and infusion rate in this example, the cooling of the tissue to twenty-eight degrees occurs in approximately sixty seconds. This time period is less than two minutes, which is generally the maximum amount of time that a tissue region should be deprived of oxygenated blood during a heart procedure. The methods of FIGS. 1 and 4 allow cooling beyond the two minute benchmark by providing cool fluid and oxygenated blood in proportions to maintain the temperature of the tissue region below normal body temperature.

Once the tissue is cooled to the low temperature in the target temperature range, the balloon may be deflated (as shown in FIG. 1B) to provide normal blood flow to the tissue region. In the FIG. 3 example, the balloon is deflated at data point 52. The flow of blood to the tissue region at normal body temperature and the heat provided by adjacent body tissues cause the temperature of the tissue region to rise. After approximately sixty seconds of normal blood flow, the temperature of the tissue region will return to normal body temperature. Thus, in implementations where the cooling of the tissue region is to be maintained for an extended period of time, such as the example of FIG. 3, normal blood flow to the tissue region is prevented once the tissue temperature rises to the high temperature of thirty-four degrees in the target temperature range 62, and cool fluid is once again provided to cool the tissue region.

In the FIG. 3 example, the inflation of the balloon and the providing of cool fluid to the tissue region occurs again at data point 54. The time elapsed between data points 52 and 54 is approximately thirty seconds. At data point 54, cool fluid is again provided to the tissue region, and the tissue is once again cooled to approximately twenty-eight degrees as indicated by data point 56. In this example, the cool fluid provided during the period between data points 54 and 56 is provided at the same temperature (fifteen degrees) and infusion rate (twenty-five ml/min) as during the initial cooling period between data points 50 and 52. In other implementations, however, the cool fluid may be provided at a different temperature and infusion rate, which may change the rate of cooling.

After the tissue region is cooled to approximately twenty-eight degrees, the balloon is deflated and normal blood flow to the tissue is resumed. The flow of blood at normal body temperature to the tissue region causes the temperature of the tissue region to rise once again. When the temperature of the tissue region increases to approximately thirty-four degrees, the balloon is inflated and normal blood flow is prevented starting at data point 58. Cool fluid is provided once again to cool the tissue region. The process of cooling and resuming normal blood flow may continue for an extended period of time. Alternatively, cool fluid could be continuously infused during the balloon inflate-deflate cycle; this would allow for less temperature variation while providing oxygenated perfusion.

The tissue cooling time may be limited by the total amount of cool fluid that is provided to tissue region during the cooling procedure. According to standard practice, the maximum amount of fluid that should be injected into the body during the procedure is approximately one liter. At the infusion rate of the cool fluid in the FIG. 3 example, the cooling procedure may be performed for approximately sixty minutes before a liter of cool fluid is provided to the body. In other implementations, the total cooling time may be extended by providing cool fluid at a temperature below fifteen degrees at a lower infusion rate. However, fluid temperatures that are too low may cause a spasm of the artery or arrhythmias. Once the tissue has been cooled for a desirable period of time, the balloon is deflated and the temperature of the tissue region will return to normal body temperature as indicated by data point 60. In some examples, cool fluid may be provided to the tissue region in addition to normal blood flow to gradually bring the temperature of the tissue region back to normal body temperature. In this example, the target warming rate is between one-half and two degrees Celsius per minute. Warming the tissue region at a rate above two degrees Celsius per minute may result in fibrillation.

Figure 4:
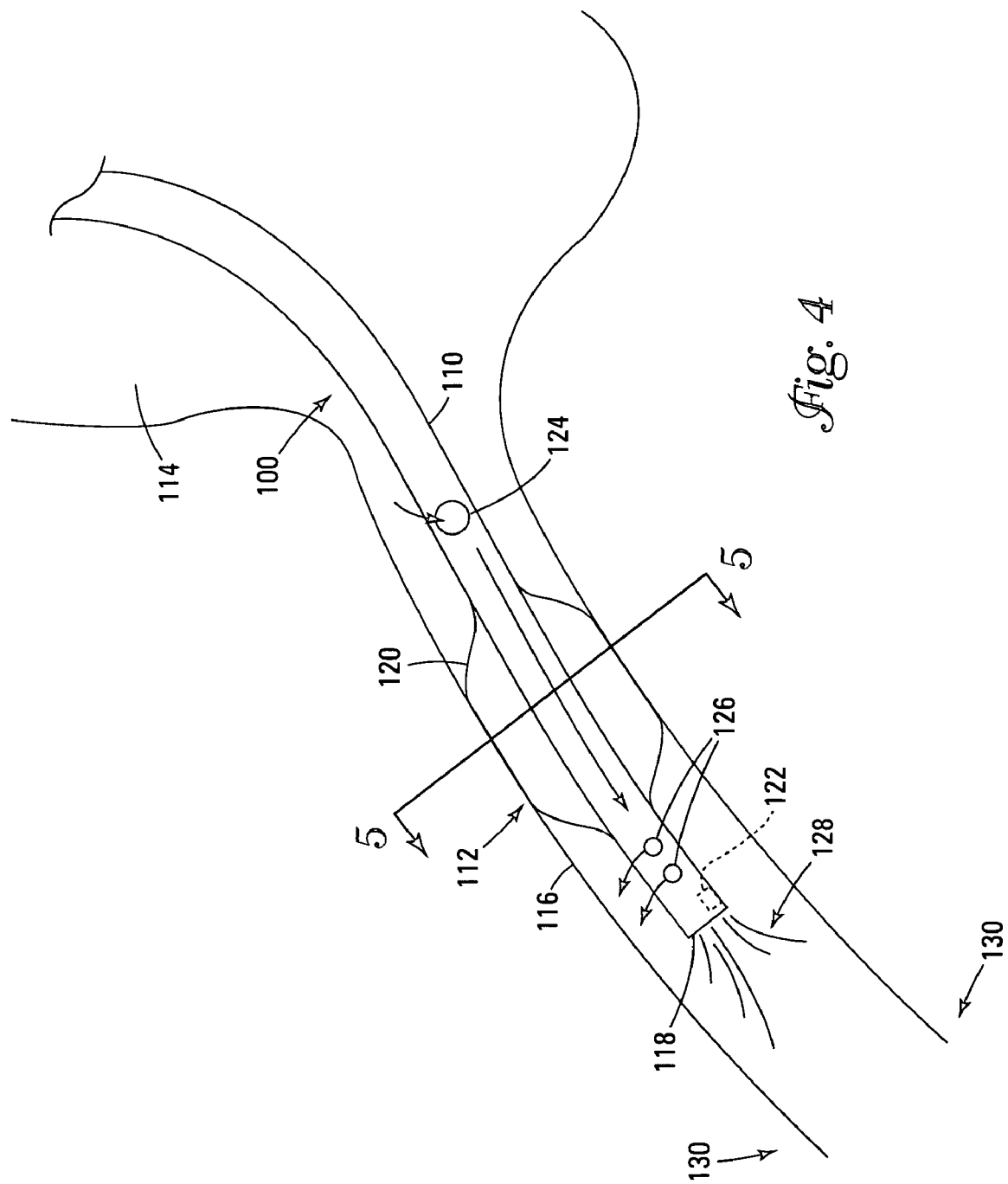
FIG. 4 is a diagram of a side view of a distal end of a perfusion catheter positioned in a coronary artery, shown in cross-section, and illustrates an alternative method of cooling a target tissue region in the heart.

FIG. 4 shows an alternative method of cooling a target tissue region inside the heart. In the FIG. 4 example, a distal portion 100 of a conventional perfusion catheter is positioned into a coronary artery 116 of the heart to cool a target tissue region 130. Once a distal end 112 of the catheter is positioned in the artery 116, a balloon 120 is inflated to prevent normal blood flow to the target tissue region 130, and in some implementations, to open an occlusion of the coronary artery 116. Cool fluid 128 is provided from an opening 118 at the catheter's distal end 112 to the target tissue region 130. Blood that enters hole 124 located proximal to the balloon 120 and that exits the catheter shaft 110 distal to the balloon 120 is also provided to the tissue region 130. By providing a mixture of cool fluid 128 and the patient's blood, the tissue region 130 may be simultaneously cooled and supplied with oxygen.

An inflation lumen (not shown) extends longitudinally through the catheter from the balloon 120 to the catheter's proximal end (not shown in FIG. 4). The balloon 120 may be inflated and deflated by providing and removing an inflation medium via the inflation lumen, as is conventional. In this implementation, the balloon 120 is a conventional balloon suited for use in the heart. For implementations in other locations inside the body, a different balloon may be used. The inflation and deflation of the balloon 20 may be controlled manually by the physician, or in some implementations, may be controlled automatically by an external control system.

An infusion lumen (the lumen being shown in FIG. 5) extends longitudinally through the catheter from an opening 118 at the catheter's distal end 112 to an opening at the catheter's proximal end (not shown). The cool fluid 128 is provided to the tissue region 130 via the catheter's infusion lumen. The cool fluid may be provided at various temperatures and infusion rates, as will be described in conjunction with FIG. 6. In one example, the catheter's infusion lumen may be twenty thousandths of an inch in diameter at the catheter's distal end 112. The twenty thousandths diameter may likely prevent the jetting effect that may occur at smaller infusion lumen diameters, as discussed previously. A physician can manually provide the cool fluid 128 to the tissue region 130, or a control system may be used.

A perfusion lumen (the lumen being shown in FIG. 5) in the catheter shaft 110 extends longitudinally through the catheter distal end 100 between the holes 124 and 126. The size and shape of the hole 124 determines the amount of blood that enters the perfusion lumen and bypasses the inflated balloon 120 as indicated by the arrows. In the FIG. 4 implementation, the perfusion lumen of catheter 100 allows blood to bypass the balloon 120 at a rate of fifteen to thirty ml/min. Because the approximate amount of blood flow to the target tissue 130 is known, an appropriate amount of cooled fluid 128 can be provided to the tissue region 130 via the inflation lumen to maintain the temperature of the tissue region 130 at a desired temperature below normal body temperature.

A temperature sensor 122 is located at the catheter's distal end 112 to sense the temperature of the cool fluid 128 as the fluid 128 exits the infusion lumen through the opening 118 and to provide feedback to the physician performing the procedure. In this example, the temperature sensor 122 is a thermocouple. In other implementations, other temperature sensors may be used, such as thermistors or other suitable temperature sensing mechanisms. Further, the temperature sensor may be extended distal to the catheter opening 118, as shown in FIGS. 1A and 1B, or positioned at other locations within the catheter shaft to measure the temperature of the fluid. In other implementations, the temperature sensor 122 may be omitted.

The perfusion catheter of the FIG. 4 example may be used to simultaneously provide cool fluid and blood to the tissue region. In other implementations, a conventional balloon catheter, such as the catheter shown in FIGS. 1A and 1B, may be used to provide the same effect. In the FIG. 1A example, the balloon 20 was inflated to completely occlude the coronary artery 16 and prevent all blood flow to the tissue region 30. If the balloon 20 were only partially inflated, a specified amount of blood could flow around the partially inflated balloon 20 and be provided to the tissue region 130.

Figure 5:
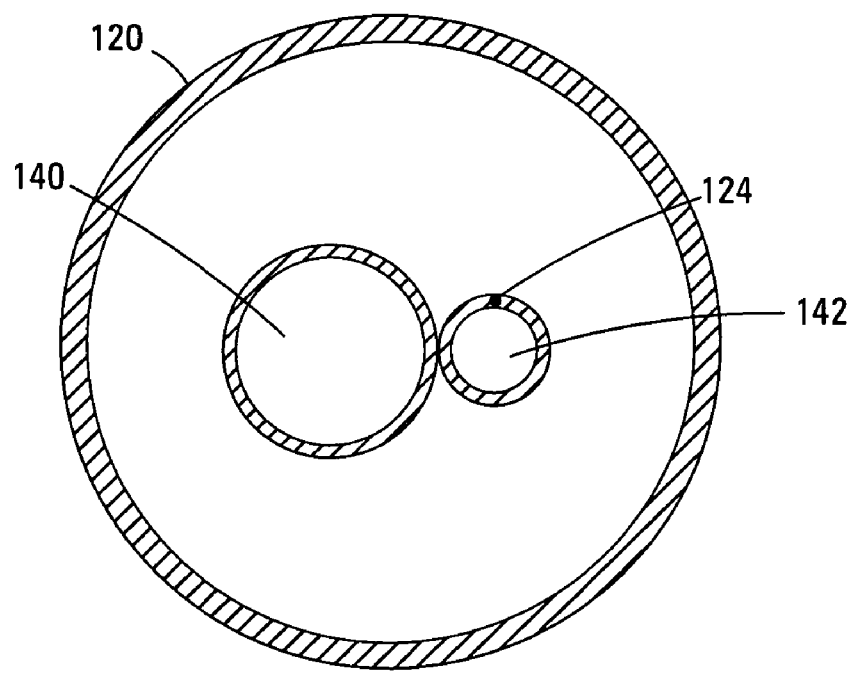
FIG. 5 is a cross-sectional view of the perfusion catheter along the line 5-5 shown in FIG. 4.

FIG. 5 is a cross-sectional view of the perfusion catheter along the line 5-5 shown in FIG. 4. The FIG. 5 cross-section illustrates the relative diameters of the lumens that extend longitudinally through the catheter and the catheter's balloon 120. In the FIG. 5 example, the catheter includes a perfusion lumen 140 and an infusion lumen 142. The perfusion lumen may have a diameter of approximately forty-seven thousandths of an inch, which perfuses blood at a rate of approximately fifteen to thirty ml/min. In other examples, a larger or smaller diameter perfusion lumen may be used to increase or decrease the amount of blood perfused to the tissue region. The infusion lumen 142 may have an inner of twenty thousandths of an inch, which would allow a physician to use an eighteen-thousandths guidewire, or a smaller guidewire if needed. In other examples, the infusion lumen 40 may have an inner diameter of eighteen thousandths of an inch or smaller.

In the FIG. 5 example, the wires 124 extending from the temperature sensor 122 (not shown in FIG. 4) are located next to the infusion lumen 142. In other examples, the catheter may include a sensor lumen, as shown in FIG. 2, or the wires 124 may extend longitudinally in a different location within the catheter. The outer diameter of the catheter shaft 110 may be sixty-five thousands of an inch. However, the catheter shaft 26 may be larger or smaller in other examples. The outer diameter of the inflated balloon 120 may be approximately three millimeters. In other implementations, a catheter having a larger or smaller diameter balloon 20 may be used.

Figure 6:
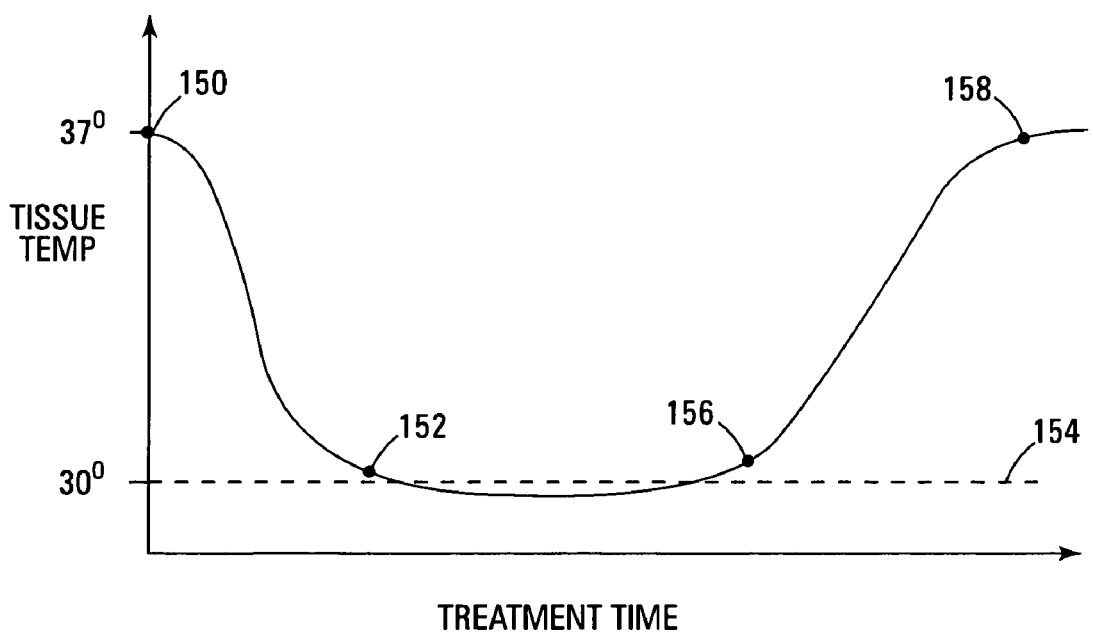
FIG. 6 is a graph that shows the temperature of the target tissue region during the application of the cooling method illustrated in FIG. 4.

FIG. 6 is a graph that illustrates the temperature of the target tissue region during the application of the cooling method of FIG. 4, for which example results are shown. The FIG. 6 graph is not based on actual results, but rather is intended to simply illustrate the cooling method more clearly. Before the cooling process is started, the target tissue region is at normal body temperature, as indicated by data point 150. In this example, the tissue region is cooled to a target temperature of thirty degrees Celsius and is maintained at that temperature for the duration of the procedure.

The cooling method of FIG. 6 begins by inflating the balloon at data point 150 to prevent normal blood flow to the tissue region. The catheter's perfusion lumen permits a controlled amount of blood to be provided to the tissue region through the hole in the catheter shaft, for example twenty ml/min. In other implementations, perfusion catheters that permit more or less blood to flow to the tissue region may be used. Once the distal end of the catheter is positioned and blood flow to the tissue region has been restricted, cool fluid is provided to the tissue region. In this example, the temperature of the cool fluid provided to the tissue region is approximately fifteen degrees Celsius and is infused at a rate of twenty-five ml/min. The mixture of cool fluid and blood cools the tissue region to approximately thirty degrees Celsius, as indicated by data point 152. At this temperature and infusion rate, the tissue will cool from normal body temperature to thirty degrees Celsius in approximately sixty seconds.

Once the tissue region is cooled to the target temperature 154, the temperature of the cool fluid provided to the tissue region may be increased to prevent further cooling below the target temperature 154. In the FIG. 6 example, the temperature of the cool fluid provided to the tissue region is increased to thirty degrees at data point 152. Alternatively, further cooling below the target tissue temperature 154 may be prevented by reducing the infusion rate of the cool fluid rather than increasing fluid temperature. In other implementations, both the temperature and the infusion rate may be adjusted.

The mixing of normal blood and cool fluid to maintain the target tissue temperature 154 may be continued for as long as desired. In some applications, however, the maximum amount of fluid that may be provided to the body during the cooling procedure is approximately one liter. At the infusion rate of the cool fluid in the FIG. 6 example, the cooling procedure may be performed for approximately forty minutes before a liter of cool fluid is provided to the body. In other implementations, the total cooling time may be extended by providing cool fluid at a lower temperature and at a lower infusion rate.

Once the tissue region has been cooled for the desired amount of time, the balloon may be deflated and normal blood flow to the tissue region may be resumed. The deflation of balloon 120 occurs at point 156 on the FIG. 6 graph. After normal blood flow is resumed, the temperature of the target tissue region rises until it reaches normal body temperature at data point 158. As discussed previously, in some examples additional cool fluid may be provided to the tissue region after resuming normal blood flow to gradually bring the temperature of the tissue region back to normal body temperature at the target warming rate.

In the examples shown in FIGS. 1-6, the temperature of the cool fluid provided to cool the tissue region may range from twelve to thirty-six degrees Celsius. Further, in the implementations where infusion lumens having a diameter of twenty thousandths of an inch are used, the fluid may be provided at an infusion rate of thirty ml/min without damaging the vessel walls. Alternatively, fluid may be provided at higher rates in implementations where the catheter includes a diffuser (i.e., holes or slots) at its distal end through which the fluid exits. The time required to cool the tissue region in the various examples may be reduced by providing fluids at lower temperatures or at higher infusion rates. Conversely, providing cool fluid at temperatures higher temperatures or lower infusion rates may increase the time required for the cool fluid to cool the tissue region. The upper and lower limit of the temperature range in the example of FIGS. 1-3 and the target temperature of the FIG. 4-6 example may be increased or decreased as desired. However, temperatures below twenty-eight degrees Celsius may cause complications such as arterial spasm or fibrillation.

The cooling methods illustrated in FIGS. 1-6 may be performed in a vessel that contains a lesion or blockage and is being treated with a percutaneous transluminal coronary angioplasty. Alternatively, the method may be performed in a vessel that does not require such treatment. For procedures where the methods are performed in a vessel that does not require the repair of a lesion, the cooling method can be utilized to cool a target tissue region that is adjacent to the tissues in fluid communication with the particular vessel in which the method is being performed. The cooling method may also be used to cool other organs in the body, such as the brain, kidney, and liver.

Figure 7:
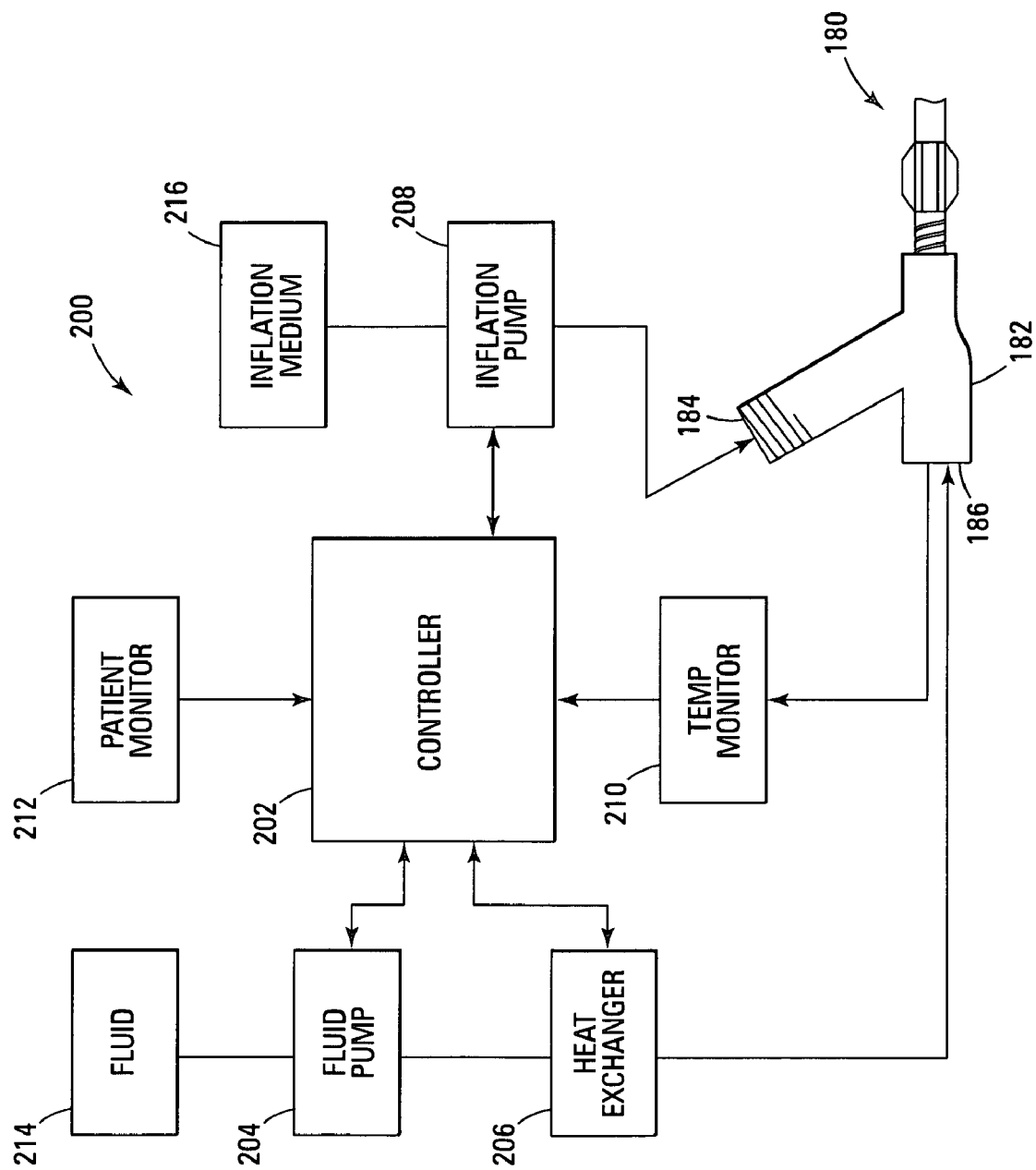
FIG. 7 is a diagram of a side view of a proximal end of a catheter used to cool a target tissue region and a control system connected to the proximal end of the catheter, the control system shown in block diagram.

The cooling methods previously described in FIGS. 1A, 1B, and 4 may be performed manually, or automatically with the aid of an external control system. FIG. 7 shows a proximal end of a catheter 180 connected to a control system 200. In this example, the control system 200 includes a controller 202, a fluid pump 204, a heat exchanger 206, an inflation pump 208, a temperature monitor 210, and a patient monitor 212. The controller 202 controls the operation of the fluid pump 204 and the heat exchanger 206, which together dictate the temperature and rate of cool fluid provided to the tissue region via catheter 180. The controller 202 also controls the inflation pump 208, which dictates the amount of normal blood flow to the tissue region by inflating and deflating the catheter's balloon. Through the control of these external devices, the controller 202 may cool the tissue region and maintain the cool temperature for an extended period of time.

Catheter 180 has an adapter 182 that has two ports 184 and 186. The port 184 provides access to an inflation lumen that extends longitudinally through the catheter to a balloon at the catheter's distal end (not shown in FIG. 7). An inflation medium may be provided to the balloon via the inflation lumen to inflate and deflate the balloon. The port 186 provides access to an infusion lumen that also extends longitudinally to an opening at the catheter's distal end. Cooled fluid may be provided to the target tissue region via the infusion lumen. In the FIG. 7 example, the catheter 180 is a balloon catheter. In other implementations, the catheter 180 may be a perfusion catheter or other catheter suitable for cooling a target tissue region in accordance with the methods described herein.

In the FIG. 7 implementation, the controller 202 receives input from the other devices in the control system 200 and uses that information, in addition to patient data input by a physician, to coordinate the providing of fluid and the flow of normal blood to the tissue region. For example, the fluid pump 204 provides the controller 202 with the rate at which the fluid 214 is infused through the catheter 180 to the tissue region. The temperature monitor 210 inputs the temperature of the fluid 214 as it exits the distal end of the catheter or the temperature of the fluid distal to the end of the catheter 180. In implementations where a temperature monitor 210 is not used, the heat exchanger 206 may provide the temperature of the fluid 214 before it is infused through the catheter 180. The inflation pump 208 provides the controller 202 with the pressure of the balloon. From the information provided by the inflation pump 208, the controller 202 can determine whether the balloon is inflated, and if so, whether the balloon is fully inflated or only partially inflated. The patient monitor 212 provides the patient's physiologic information to the controller 202, such as the patient's heart rate, heart rhythm, blood pressure, blood oxygen level, etc. From this information, the controller 202 can alert the physician if the patient is experiencing complications and may adjust the cooling procedure accordingly.

The controller 202 may also receive information about the procedure to be performed, such as the specific cooling technique to be applied, the type of catheter that is being used (including the diameter of the inflation lumen and size of the balloon), the vessel in which the cooling technique will be applied, the type of fluid that is being provided to the target tissue region, the target temperature range, the total length of the procedure, and the total volume of fluid to be infused. In certain applications, the temperature of the target tissue region cannot be directly measured during the cooling procedure. This is often the case when the target tissue region cannot be readily accessed without performing a more invasive procedure. In implementations where the temperature of the tissue region can be measured during the cooling procedure, the control system 200 may include a second temperature monitor that provides the temperature of the target tissue region to the controller 202.

In implementations where the temperature of the target tissue region cannot be measured, the controller 202 may be provided with control data obtained from bench or preclinical testing that allows the controller 202 to determine the temperature of the target tissue region based on the temperature and infusion rate of the fluid 214 and the amount of normal blood flow provided to the tissue region. For example, the control data may include the rate of temperature changes in an assortment of tissue regions inside the body when cool fluids are provided at varied temperatures and infusion rates. This information may be provided to the controller 202 for a variety of different fluids that may be used to cool the body. The control data may also include the rate of temperature change in the tissue region when normal blood flow is provided or when only heat from surrounding tissue is provided to the tissue region. Parameters for cycling the inflation of the balloon during the various stages of the cooling procedure to provide normal blood flow to the tissue region may also be included.

The control data may also include procedural constraints, such as a minimum temperature of the target tissue region and the maximum rate at which the tissue region may be cooled or allowed to warm. With respect to the control of the catheter's balloon, the control data may indicate the size of the various body vessels and the required pressure to properly inflate the balloon. Additionally, the maximum infusion rate and total amount of a cool fluid injected into the body during a procedure may also be provided. These are only some examples of the information that may be provided to the controller 202 in the form of control data to control the cooling of the target tissue region. Other data may be provided as necessary.

After receiving the patient data and the inputs from the other devices in the control system 200 described above, the controller 202 processes this information in accordance with the control data previously described and provides output to the fluid pump 204, the heat exchanger 206, and the inflation pump 208 to control the temperature of the tissue region. During the procedure, the controller 202 continually monitors these inputs and adjusts the outputs in accordance with the cooling procedure being performed. In the FIG. 7 implementation, the controller 202 is a digital or analog feedback controller. In other implementations, a different type of controller may be used.

In the FIG. 7 implementation, the fluid used for infusion is fluid 214. However, any fluid that is biocompatible may be infused for cooling. Additionally, the fluid 214 may contain additives and may be changed throughout the cooling procedure. The fluid 214 may be infused through the infusion lumen of the catheter by a conventional pump 204. For example, a positive displacement pump may be used to provide the pressure necessary to urge the fluid 214 through the narrow infusion lumen of the catheter. In other implementations the pump 204 may be replaced with a raised bag containing the fluid 214 with an inflatable pressure cuff to control the infusion rate of the fluid 214. The fluid pump 204 includes an infusion monitor to monitor the pressure and flow rate of the fluid 214 through the infusion lumen of the catheter 180 and provide that information to the controller 202.

A conventional heat exchanger may be used to cool the fluid 214. In this implementation, the heat exchanger is controlled by the controller 202 by processing the information received from the temperature monitor 210 and the controller's control data. The temperature monitor 210 receives information from a temperature sensor in the catheter, such as the temperature sensor 22 shown in FIG. 1A, or the temperature sensor 122 shown in FIG. 4. Based on the information provided by the temperature monitor 210, the heat exchanger 206 can be used to cool or warm the fluid 214 provided to the target tissue region. In implementations where a temperature sensing device is not used to measure the temperature of the fluid 214 provided to the tissue region, the temperature monitor 210 may be omitted.

The inflation medium 216 may be infused through the inflation lumen of the catheter by a conventional pump 208. The inflation medium may be either a gas or a liquid. In one implementation, the inflation pump 208 is a positive displacement pump. In other implementations, the pump 208 may be a pneumatic or hydraulic pump. In implementations where the catheter's balloon is not inflated and deflated to control the flow of blood to the tissue region, such as the method shown in FIGS. 4 and 5, the inflation pump may be omitted and the inflation and deflation of the balloon may be performed manually.

A number of embodiments of the invention have been described. Nevertheless, it will be understood that various modifications may be made without departing from the spirit and scope of the invention. Accordingly, other embodiments are within the scope of the following claims.

What is claimed is:

1. A method of cooling a target tissue region inside a human body, the method comprising:
providing non-oxygenated fluid cooled below normal human body temperature of about 37 degrees Celsius and oxygenated blood at a normal human body temperature of about 37 degrees Celsius to the tissue region in proportions to cool the tissue region and maintain, for an extended period of time greater than two minutes, the temperature of the tissue region within a target temperature range that is one to nine degrees Celsius below the normal body temperature, wherein the oxygenated blood is provided so that any continuous period of time during which the tissue region is deprived of oxygenated blood while the non-oxygenated fluid is being provided continues for less than two minutes, and further wherein the providing of the blood at the normal body temperature to the tissue region is performed using a catheter that occludes a vessel upstream from the tissue region and permits a selected amount of blood to flow through a lumen in the catheter and to the tissue region.

2. The method of claim 1 wherein the cooled fluid and the blood at normal body temperature are provided to the tissue region simultaneously.

3. The method of claim 1 wherein the catheter also performs the providing of cool fluid to the tissue region.

4. The method of claim 1 wherein a catheter positioned in a vessel in fluid communication with the tissue region provides the fluid to the tissue region through a lumen that extends longitudinally through the catheter, the lumen having a diameter of at least twenty thousandths of an inch.

5. The method of claim 1 wherein the temperature of the tissue region is maintained within the target temperature range that is below normal body temperature for a time period beyond the normal length of time a tissue region is deprived of oxygenated blood during a head procedure.

6. The method of claim 5 wherein the normal length of time a tissue region is deprived of oxygenated blood during a heart procedure is about two minutes.

7. The method of claim 1 wherein the temperature of the tissue region is maintained within the target temperature range for at least about two minutes.

8. The method of claim 1 wherein the providing of fluid and blood to cool the target tissue region is performed during a procedure to open a lesion in a vessel.

9. The method of claim 1 wherein a control system controls the providing of fluid and blood to the tissue region.

10. A method of cooling a target tissue region inside a human body, the method comprising:
occluding a human body vessel to prevent normal blood flow to the tissue region;
providing, while the body vessel is occluded, cooled fluid to the tissue region to cool the tissue region below normal body temperature of about 37 degrees Celsius;
recommencing normal blood flow to the tissue region by removing the occlusion in the body vessel;
preventing normal blood flow to the tissue region again by occluding the body vessel before the temperature of the tissue region returns to normal body temperature; and
providing, while the body vessel is occluded, cooled fluid to the tissue region again to maintain the temperature of the tissue region below the normal body temperature of about 37 degrees Celsius.

11. The method of claim 10 wherein the body vessel is occluded to prevent normal blood flow to the tissue region by inflating a balloon positioned in the vessel.

12. The method of claim 10 wherein a catheter positioned in a vessel at a location upstream from the tissue region provides the fluid to the tissue region through a lumen extending longitudinally through the catheter, the lumen having a diameter of at least twenty thousandths of an inch.

13. The method of claim 10 wherein a control system controls the occluding of the body vessel and the providing of cooled fluid to the tissue region to maintain the temperature of the tissue region below normal body temperature.

14. A method of cooling a target tissue region inside a human body, the method comprising:
restricting normal blood flow to the tissue region so that only a desired amount of blood is provided to the tissue region; and
providing cool fluid to mix with the blood provided to the tissue region so as to cool the tissue region below normal body temperature of about 37 degrees Celsius and to maintain, for an extended period of time greater than two minutes, the temperature of the tissue region within a target temperature range that is one to nine degrees Celsius below the normal body temperature of about 37 degrees Celsius, further wherein the providing of the blood at normal body temperature to the tissue region is performed using a catheter that occludes a vessel upstream from the tissue region and permits a selected amount of blood to flow through a lumen in the catheter and to the tissue region.

15. The method of claim 14 wherein the temperature of the tissue region is maintained within the target temperature range that is below the normal body temperature for a time period beyond the normal length of time a tissue region is deprived of oxygenated blood during a heart procedure.

16. The method of claim 15 wherein the normal length of time a tissue region is deprived of oxygenated blood during a heart procedure is about two minutes.

17. The method of claim 14 wherein the temperature of the tissue region is maintained within the target temperature range for at least about two minutes.

18. The method of claim 14 wherein a catheter positioned in a vessel in fluid communication with the tissue region provides the fluid to the tissue region through a lumen that extends longitudinally through the catheter, the lumen having a diameter of at least twenty thousandths of an inch.

19. The method of claim 14 wherein a control system controls the providing of fluid to the tissue region to maintain the temperature of the tissue region below normal body temperature.

20. A method of cooling a target tissue region inside a human body, the method comprising:
providing non-oxygenated fluid cooled below normal human body temperature of about 37 degrees Celsius and oxygenated blood at the normal human body temperature of about 37 degrees Celsius to the tissue region in proportions to cool the tissue region and maintain, for an extended period of time greater than two minutes, the temperature of the tissue region within a target temperature range that is one to nine degrees Celsius below the normal human body temperature of about 37 degrees Celsius, wherein the oxygenated blood is provided so that any continuous period of time during which the tissue region is deprived of oxygenated blood while the non-oxygenated fluid is being provided continues for less than two minutes, and further wherein the providing of the blood at the normal body temperature to the tissue region is performed by occluding a vessel upstream from the tissue region to restrict normal blood flow and then removing the occlusion to permit normal blood flow.

21. The method of claim 20 wherein the cooled fluid and the blood at normal body temperature are provided to the tissue region simultaneously.

22. The method of claim 20 wherein the catheter also performs the providing of cool fluid to the tissue region.

23. The method of claim 20 wherein a catheter positioned in a vessel in fluid communication with the tissue region provides the fluid to the tissue region through a lumen that extends longitudinally through the catheter, the lumen having a diameter of at least twenty thousandths of an inch.

24. The method of claim 20 wherein the temperature of the tissue region is maintained within the target temperature range that is below normal body temperature for a time period beyond the normal length of time a tissue region is deprived of oxygenated blood during a heart procedure.

25. The method of claim 24 wherein the normal length of time a tissue region is deprived of oxygenated blood during a heart procedure is about two minutes.

26. The method of claim 20 wherein the temperature of the tissue region is maintained within the target temperature range for at least about two minutes.

27. The method of claim 20 wherein the providing of fluid and blood to cool the target tissue region is performed during a procedure to open a lesion in a vessel.

28. The method of claim 20 wherein a control system controls the providing of fluid and blood to the tissue region.

* * * * *

UNITED STATES PATENT AND TRADEMARK OFFICE
CERTIFICATE OF CORRECTION

PATENT NO.          : 7,326,195 B2
APPLICATION NO.     : 10/715636
DATED               : February 5, 2008
INVENTOR(S)         : Martin Willard and Kent Harrison It is certified that error appears in the above-identified patent and that said Letters Patent is hereby corrected as shown below:

Column 13, line 66 through Column 14, line 3, please delete "wherein a catheter positioned in a vessel in fluid communication with the tissue region provides the fluid to the tissue region through a lumen that extends longitudinally through the catheter, the lumen having a diameter of at least twenty thousandths of an inch" and insert --wherein the lumen has a diameter of at least twenty thousandths of an inch-- therefor;

Column 14, line 8, please delete "head" and insert --heart-- therefor;

Column 15, lines 10-14, please delete "wherein a catheter positioned in a vessel in fluid communication with the tissue region provides the fluid to the tissue region through a lumen that extends longitudinally through the catheter, the lumen having a diameter of at least twenty thousandths of an inch" and insert --wherein the lumen has a diameter of at least twenty thousandths of an inch-- therefor;

Column 16, line 11-15, please delete "wherein a catheter positioned in a vessel in fluid communication with the tissue region provides the fluid to the tissue region through a lumen that extends longitudinally through the catheter, the lumen having a diameter of at least twenty thousandths of an inch" and insert --wherein the lumen has a diameter of at least twenty thousandths of an inch-- therefor.

Signed and Sealed this

Nineteenth Day of August, 2008

JON W. DUDAS
*Director of the United States Patent and Trademark Office*